(12) United States Patent
Seo et al.

(10) Patent No.: US 7,078,114 B2
(45) Date of Patent: Jul. 18, 2006

(54) PHOSPHORESCENCE COMPOUND AND ELECTRO FIELD LIGHT EMITTING DEVICE HAVING THE SAME

(75) Inventors: Satoshi Seo, Kanagawa (JP); Hideko Inoue, Kanagawa (JP); Atsushi Tokuda, Kanagawa (JP); Ryoji Nomura, Kanagawa (JP)

(73) Assignee: Semiconductor Energy Laboratory Co., Ltd. (JP)

( * ) Notice: Subject to any disclaimer, the term of this patent is extended or adjusted under 35 U.S.C. 154(b) by 0 days.

(21) Appl. No.: 10/719,808

(22) Filed: Nov. 21, 2003

(65) Prior Publication Data

US 2005/0112400 A1 May 26, 2005

(30) Foreign Application Priority Data

Nov. 26, 2002 (JP) ............................. 2002-342647

(51) Int. Cl.
C09K 11/06 (2006.01)
H05B 33/14 (2006.01)

(52) U.S. Cl. ...................... 428/690; 428/917; 313/504; 252/301.16; 549/3; 546/5; 546/10; 548/403

(58) Field of Classification Search ................ 428/690, 428/917; 313/504, 506; 257/40; 549/3; 252/301.16; 546/5, 10; 548/403
See application file for complete search history.

(56) References Cited

FOREIGN PATENT DOCUMENTS

JP          2002-319488        10/2002

OTHER PUBLICATIONS

Tang, C.W. et al, "Organic Electroluminescent Diodes," Applied Physics Letters, vol. 51, No. 12, pp. 913-915, Sep. 21, (1987).
Tsutsui, T., "The Operation Mechanism and the Light Emission Efficiency of the Organic EL Element," Textbook of the 3rd Seminar at Division of Organic Molecular Electronics and Bioelectronics, The Japan Society of Applied Physics, pp. 31-37, (English translation, pp. 1-11), (1993).
Inoue, H. et al, "A Reaction of Singlet Oxygen with an Unsaturated Organic Molecule," 6.1, Quencher and Photosensitizer, *Basic Chemistry Course Photochemistry I*, pp. 106-110, Maruzen Co., Japan, (1999).
O'Brien, D.F. et al, "Improved Energy Transfer in Electrophosphorescent Devices," Applied Physics Letters, vol. 74, No. 3, pp. 442-444, Jan. 18, (1999).
Tsutsui, T. et al, "High Quantum Efficiency in Organic Light-Emitting Devices with Iridium-Complex as a Triplet Emissive Center," Japanese Journal of Applied Physics, vol. 38, part 2, No. 12B, pp. L1502-L1504, Dec. 15, (1999).
Baldo, M.A. et al, "High-Efficiency Fluorescent Organic Light-Emitting Devices Using a Phosphorescent Sensitizer," Nature, (London) vol. 403, pp. 750-753, Feb. 17, (2000).
Thompson, M.E. et al, "Phosphorescent Materials and Devices," The 10th International Workshop on Inorganic and Organic Electroluminescence, (EL '00) pp. 35-38, (2000).
Anderson, C. et al, "Oxidative Addition of Alkyl Halides to Chiral Cyclometallated Platinum(II) Complexes with Thienyl Imines. X-ray Crystal Structure of [PtMe{3-((S)-PhCHMeNCH)C$_4$H$_2$S}SMe$_2$]," Journal of Organometallic Chemistry, vol. 604, pp. 178-185, (2000).

(Continued)

*Primary Examiner*—Marie Yamnitzky
(74) *Attorney, Agent, or Firm*—Cook, Alex, McFarron, Manzo, Cummings & Mehler, Ltd.

(57) ABSTRACT

A phosphorescent compound is formed by synthesizing an orthometallated complex by using easily-synthesized ligands. An electroluminescent device having high luminous efficiency uses the phosphorescent compound. Moreover, a light-emitting device operating at a low voltage uses the electroluminescent device. A phosphorescent compound represented by general formula [formula 1] is synthesized. Further, an electroluminescent device containing the phosphorescent compound is formed. In order to generate phosphorescent emission more efficiently, a heavy metal is preferably used as a central metal from the perspective of heavy atom effects. Therefore, one feature of the present invention is that the central metal M in the below general formula [formula 1] is iridium or platinum

[formula 1]

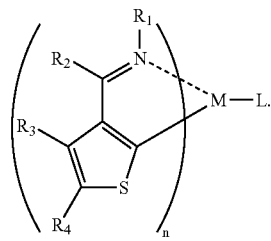

15 Claims, 5 Drawing Sheets

OTHER PUBLICATIONS

International Search Report for application No. PCT/JP03/14816, dated Mar. 16, 2004 (In Japanese).

International Preliminary Examination Report for application No. PCT/JP03/14816, dated Jun. 15, 2004, (In Japanese)—with partial English translation.

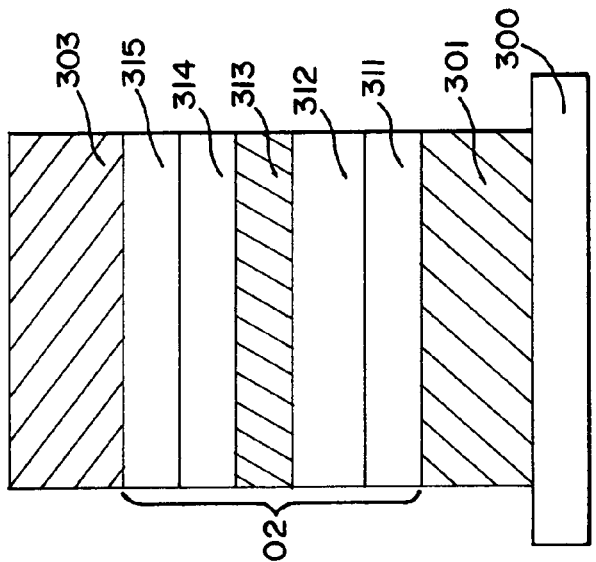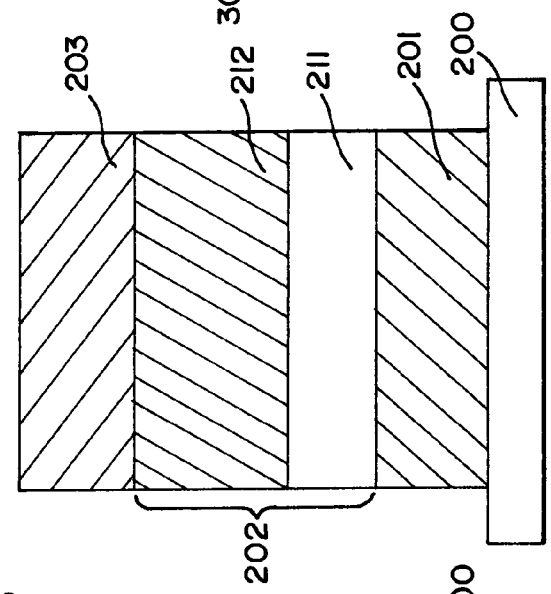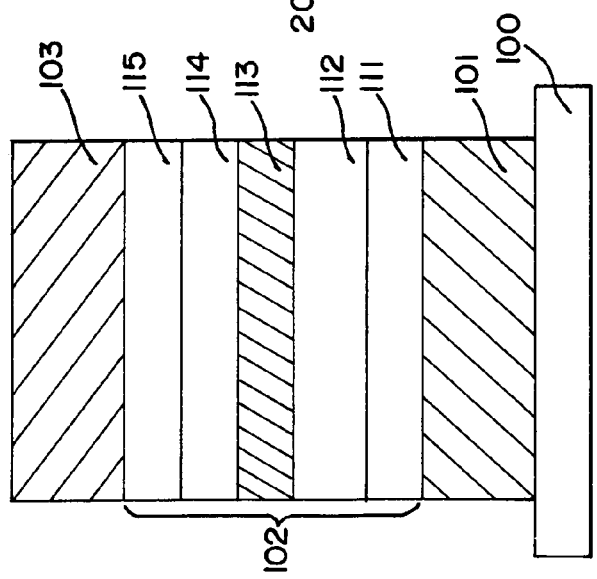

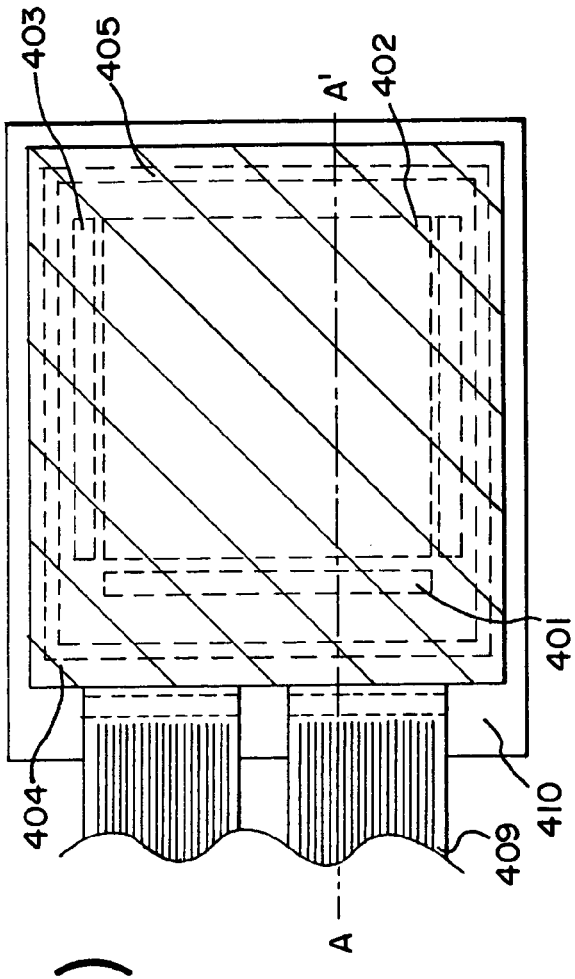
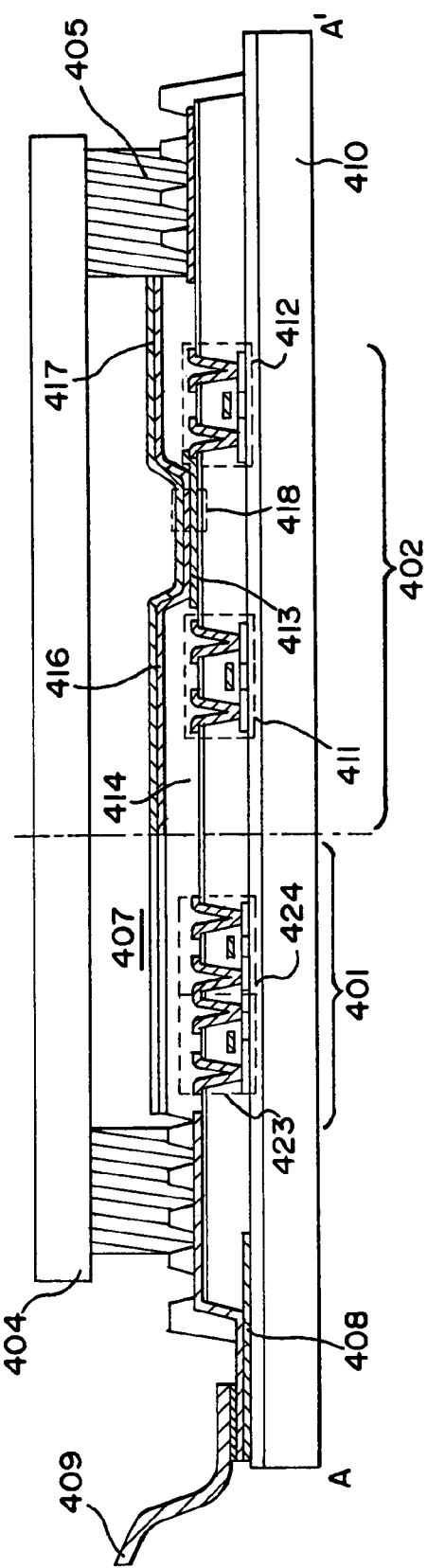
FIG.4(A)
FIG.4(B)

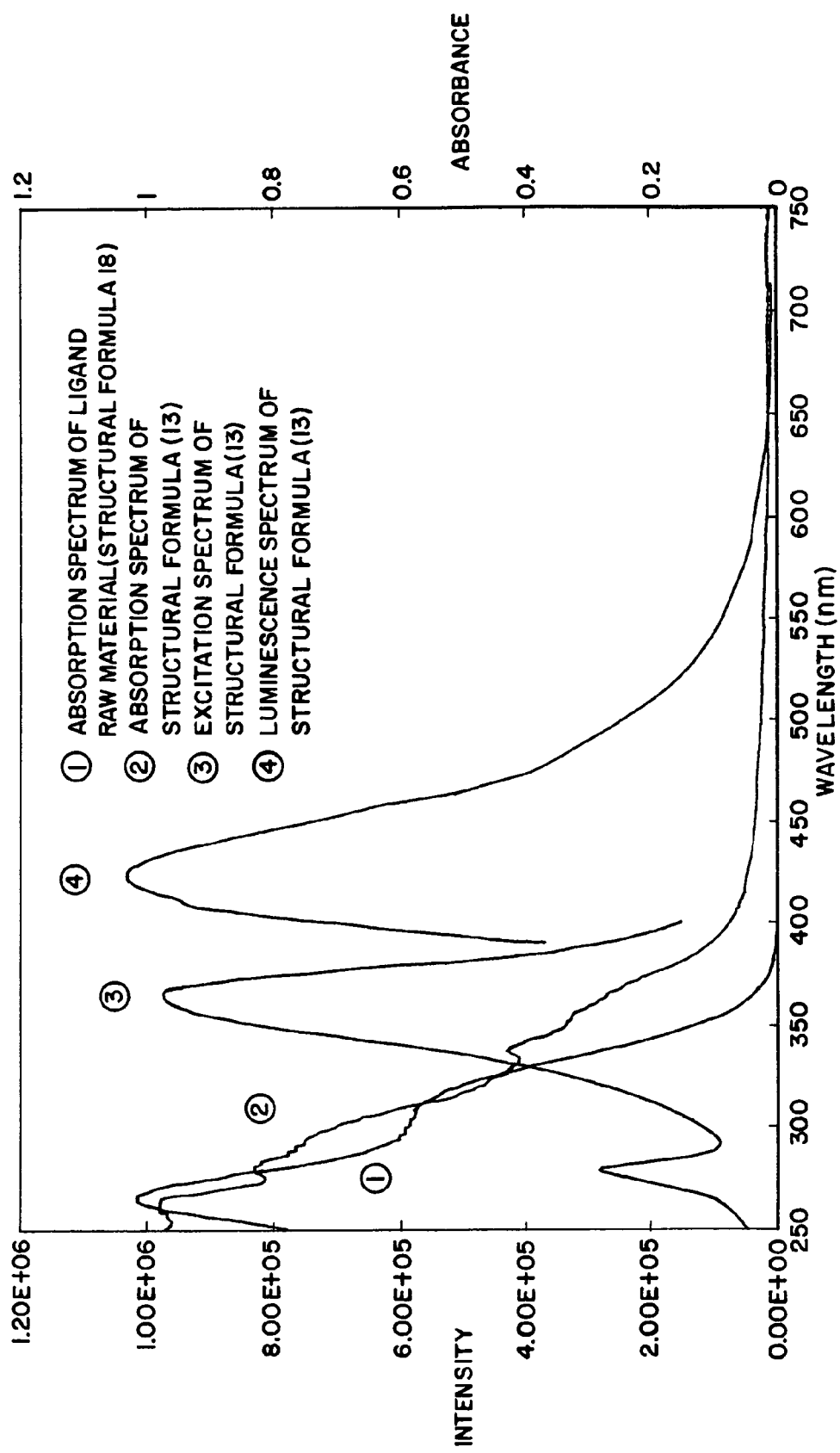

PHOSPHORESCENCE COMPOUND AND ELECTRO FIELD LIGHT EMITTING DEVICE HAVING THE SAME

BACKGROUND OF THE INVENTION

1. Field of the Present Invention

The present invention relates to the compound in which light emission is generated through the triplet excited state (hereinafter, phosphorescent compound). Further, the invention relates to an electroluminescent device having an anode, a cathode, and a layer containing an organic compound in which light is generated when an electric field is passed through the layer (hereinafter, electroluminescent layer) and phosphorescent compounds are contained, and a light-emitting device having the electroluminescent device.

2. Description of the Related Art

Organic compounds (an organic molecule) undergo transitions to the energy state having the highest energy (excited state) when they absorb light. Through the excited state, various reactions (photochemical reactions) or luminescence may occur. Hence, there are many applications of the organic compounds.

A reaction of singlet oxygen with unsaturated organic molecules (oxygen addition) is an example of a photochemical reaction. For example, refer to Haruo INOUE, Katsuhiko TAKAGI, Masako SASAKI, and Syosinn BOKU, "Basic Chemistry Course PHOTOCHEMISTRY I", Maruzen Corporation, pp. 106–110 (1999). Since the ground state of oxygen molecules is a triplet state, singlet state oxygen (singlet oxygen) is not produced by direct photoexcitation. However, in the presence of another triplet excited molecule, singlet oxygen can be produced, and it causes an oxygen addition reaction. Here, compounds capable of producing the foregoing triplet excited molecules are referred to as a photosensitizer.

As stated above, in order to produce singlet oxygen, a photosensitizer capable of producing triplet excited molecules by photoexcitation is required. However, since the ground state of general organic compounds is a singlet state, the photoexcitation to a triplet excited state is a forbidden transition, that is, the probability of generating triplet excited molecules is very small (generally, singlet excited molecules are generated). Therefore, as the photosensitizer, the compounds that are subjected to intersystem crossing between a singlet excited state and a triplet excited state are required. In other words, such compounds are beneficial in use as a photosensitizer.

Further, the compounds that are subjected to intersystem crossing may emit phosphorescence. Phosphorescence is the light emission that occurs from a transition between electronic states of different multiplicities, that is, the light emission occurs from a transition from the triplet excited state back down to the singlet ground state in typical organic compounds. (Further, fluorescence is the light emission that occurs from a transition from the singlet excited state back to the singlet ground state.) Compounds capable of emitting phosphorescence (phosphorescent compound) can be applied to an electroluminescent device containing organic compounds as light-emitting compounds (a device in which light is emitted when an electric field is passed through the device), for example.

When an organic compound is used as a light emitter, the emission mechanism of an electroluminescent device is a carrier injection type. That is, a voltage is applied to an electroluminescent layer interposed between a pair of electrodes, and electrons injected from a cathode and holes injected from an anode are recombined with each other within the electroluminescent layer to produce excited molecules (hereinafter, molecular exciton), then, the molecular exciton radiates energy while returning to the ground state to emit light.

In such an electroluminescent device, an electroluminescent layer is formed generally to have a thin film thickness less than 1 µm. An electroluminescent device does not require backlight, which is used for the conventional liquid crystal display device, since an electroluminescent layer emits light itself, that is, the electroluminescent device is a self-luminous device. Therefore, it is highly advantageous that an electroluminescent device can be fabricated to have extremely thin film thickness and be lightweight.

In an electroluminescent layer with a thickness of about 100–200 nm, it takes several (approximately ten) nanoseconds for the process from injection to recombination of carriers in the light of the carrier mobility. Hence, the time required for the process from injection of carriers to light emission of the electroluminescent layer is on the order of a microsecond even including the process of recombination of carriers. Thus, an extremely high response speed is also one of the advantages.

Further, since an electroluminescent device is a light-emitting device of a carrier injection type, it can be operated at a direct current voltage, thereby noise is hardly generated. With respect to a driving voltage, an electroluminescent layer is formed into an even ultra thin film with a thickness of approximately 100 nm, and an electrode material is selected so as to reduce a carrier injection barrier to the electroluminescent layer. Further, a hetero structure (two-layers structure) is employed. Accordingly, a sufficient luminance of 100 cd/m$^2$ can be obtained at an applied voltage of 5.5 V. For example, refer C. W. Tang and S. A. VanSlyke, "Organic electroluminescent diodes", Applied Physics Letters, vol. 51, No. 12, 913–915 (1987).

An electroluminescent device has attracted attention as a flat panel display device of a next generation in terms of its characteristics such as thin shape and lightweight, high response speed, direct current low voltage operation, or the like. In addition, an electroluminescent device is a self luminous device, has a wide viewing angle, and has high level of visibility so that it is considered that the electroluminescent device can be used effectively as a device for the display screen of a portable device.

Further, emission observed in an electroluminescent device is the emission phenomenon which occurs from the transition of a molecular exciton back down to the ground state. Here, a singlet excited state (S*) and a triplet excited state (T*) are examples of types of the molecular exciton formed by an organic compound, which is the same as in the case of photoexcitation. In addition, their statistic generation ratios in an electroluminescent device are considered to be S*:T*=1:3. For example, refer to Tetsuo TSUTSUI, "Textbook of the 3rd seminar at Division of Organic Molecular Electronics and Bioelectronics, The Japan Society of Applied Physics", p. 31 (1993).

However, light emission (phosphorescence) from a triplet excited state is not observed in typical organic compounds at room temperature. Generally, only light emission from a singlet excited state (fluorescence) is observed. Since the ground state of an organic compound is generally a singlet ground state ($S_0$), the transition of T* to $S_0$ (phosphorescence process) is an intense forbidden transition, and the transition of S* to $S_0$ (fluorescence process) is an allowed transition. That is, light emission generally occurs from only a singlet excited state.

Therefore, the theoretical limit of internal quantum efficiency (the number of photons released per carriers injected) of an electroluminescent device is considered to be 25% based on the fact that S*:T*=1:3.

Also, light generated is not entirely emitted to the outside, and a part of the light cannot be extracted because of component materials of an electroluminescent device (electroluminescent layer materials, electrode materials) or the substrate materials-specific refractive index. The efficiency of extraction of generated light is referred to as light extraction efficiency. The light extraction efficiency of an electroluminescent device having a glass substrate is said to be approximately 20%.

For these reasons, even if all injected carriers form molecular exciton, the theoretical limit of the ratio of photons extracted finally emitted to the outside to the number of injected-carriers (hereinafter, external quantum efficiency) has been said to be 25%×20%=5%. That is, even if all carriers are recombined, only 5% thereof can be extracted as light emission.

However, in recent years, an electroluminescent device in which energy released from a transition of a triplet excited state (T*) back down to the ground state (hereinafter, triplet excited energy) can be converted into light emission has been reported successively. The high luminous efficiency has attracted attention. For example, refer to D. F. O'Brien, M. A. Baldo, M. E. Thompson and S. R. Forrest, "Improved energy transfer in electroluminescent devices", Applied Physics Letters, vol. 74, No. 3, 442–444 (1999), referred to herein as "O'Brien et al." For another example, refer to Tetsuo TSUTSUI, Moon-Jae YANG, Masayuki YAHIRO, Kenji NAKAMURA, Teruichi WATANABE, Taishi TSUJI, Yoshinori FUKUDA, Takeo WAKIMOTO and Satoshi MIYAGUCHI, "High Quantum Efficiency in Organic Light-Emitting Devices with Iridium-Complex as a Triplet Emissive Center", Japanese Journal of Applied Physics, Vol. 38, pp. L1502–L1504 (1999), referred to herein as "Tsutsui et al. (vol. 38)."

In O'Brien et al., a porphyrin complex containing platinum as a central metal is used. In Tsutsui et al. (vol. 38), an organometallic complex containing iridium as a central metal is used. Both of the complexes are phosphorescent compounds containing 3rd transition series elements as central metals. Some of them have a phosphorescent compound having external quantum efficiency beyond the above mentioned theoretical limit value, 5%.

Further, a layer comprising an organometallic complex (iridium complex) containing iridium as a central metal and a layer comprising DCM2, a known fluorescent compound, are stacked alternately to transfer triplet excited energy generated in the iridium complex into the DCM2. Consequently, light emission of the DCM2 also can be excited, as in M. A. Baldo, M. E. Thompson and S. R. Forrest, "High-efficiency fluorescent organic light-emitting devices using a phosphorescent sensitizer", Nature (London), vol. 403, 750–753 (2000), referred to herein as "Baldo et al." Light emission of DCM2 is the light emission (fluorescence) occurring from a singlet excited state. The electroluminescent device having the foregoing device configuration has the advantage that triplet excited energy of an iridium complex generated efficiently can be utilized for singlet excited energy of the DCM2 which is another molecule. As one might say, the iridium complex used as a phosphorescent compound serves as the above-mentioned photosensitizer to increase the ratio of singlet excited state of the DCM2.

As disclosed in O'Brien et al., Tsutsui et al. (vol. 38) and Baldo et al., the organic compounds in which light emission is generated through the triplet excited state, that is, an electroluminescent device containing phosphorescent compounds can achieve higher external quantum efficiency than that of the conventional device. High external quantum efficiency leads to improved luminance. Therefore, an electroluminescent device containing phosphorescent compounds will play a great role in the development of an electroluminescent device in the future as means for improving luminance and luminous efficiency.

Accordingly, phosphorescent compounds are expected to be used as a photosensitizer or a material for an electroluminescent device because the phosphorescent compounds are subject to intersystem crossing and emit light (phosphorescence) from the triplet excited state. However, the number of applicable phosphorescent compounds is few under the existing circumstance.

An iridium complex, in a few phosphorescent compounds, disclosed in Tsutsui et al. (vol. 38) or Baldo et al., is one type of organometallic complexes referred to as an orthometallated complex. The iridium complex has a phosphorescence lifetime of several hundred nanoseconds and high phosphorescence quantum efficiency so that the decrease in efficiency as luminance is improved is less than that of the porphyrin complex. With such a perspective, the orthometallated complex containing such a heavy metal serves as a guide to synthesize phosphorescent compounds.

The structure of the ligand of the iridium complex disclosed in Tsutsui et al. (vol. 38), which is comparatively simple and gives green emission with good color purity, should be altered in order to vary the emission color to another. For example, it is disclosed that some emission colors were achieved by synthesizing various ligands and iridium complexes containing the foregoing various ligands in M. Thompson, S. Lamansky, P. Djurovich, D. Murphy, F. Abdel-Razzaq, S. R. Forrest, M. Baldo, P. E. Burrows, C. Adachi, T. X. Zhou and J. J. Brown, "Phosphorescent Materials and Devices", The $10^{th}$ International Workshop on Inorganic and Organic Electroluminescence (EL '00), 35–38.

In addition, many of the foregoing ligands have difficulty in synthesis or the number of processes for the synthesis is large, and it causes an increase of cost. In order to emit phosphorescence in an orthometallated complex, it is necessary to use iridium or platinum as a central metal; however, these metal materials are expensive, and it causes an increase of cost of the ligands eventually. Further, blue emission with good color purity has not been realized yet.

Therefore, it is required to explore various emission colors by synthesizing a novel orthometallated complex (phosphorescent compound) by using ligands that can be synthesized easily.

SUMMARY OF THE INVENTION

It is an object of the present invention to provide a novel phosphorescent compound by synthesizing an orthometallated complex by using easily-synthesized ligands. A further object of the invention is to provide an electroluminescent device having high luminous efficiency by manufacturing the electroluminescent device by using the phosphorescent compounds. A still further object of the invention is to provide a light-emitting device operating at a low voltage by manufacturing the light-emitting device by using the electroluminescent device.

With a result of the inventors' earnest consideration, they focused on the fact that an orthometallated complex (one type of cyclometallated complexes) having an element of group 9 and group 10 in the periodic table as a central metal can be formed using the ligand represented by the following general formula [formula 9]:

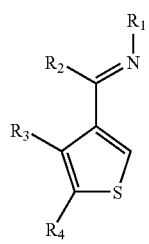

[formula 9]

The inventors found that a complex represented below by general formula [formula 1] synthesized by orthometallation (one type of cyclometallation) of the ligand represented by general formula [formula 9] generates phosphorescence. The orthometallated complex has the possibility of being synthesized at low cost in the future since the ligand represented by general formula [formula 9] can be synthesized fairly easily.

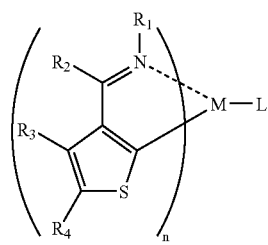

[formula 1]

wherein $R_1$ is an alkyl group, an aryl group, a substituted aryl group, a heterocyclic group, or a substituted heterocyclic group. Also, $R_2$ is hydrogen, an alkyl group, an aryl group, a substituted aryl group, a heterocyclic group, or a substituted heterocyclic group. Also, $R_3$ and $R_4$, each of which may be the same or different, are individually hydrogen, a halogen element, an alkyl group, an alkoxy group, an aryl group, a substituted aryl group, a heterocyclic group, or a substituted heterocyclic group. Also, M is at least one element of group 9 in the periodic table or at least one element of group 10 in the periodic table. When the M is at least one element of group 9 in the periodic table, n=2. When the M is at least one element of group 10 in the periodic table, n=1. L is a monoanionic ligand having a β-diketone structure, a monoanionic bidentate chelate ligand having a carboxyl group, or a monoanionic bidentate chelate ligand having a phenolic hydroxyl group.

Therefore, an aspect of the invention is to provide the phosphorescent compound represented by general formula [formula 1].

Note that in order to emit phosphorescence further efficiently, a heavy metal is preferably used as a central metal from the perspective of heavy atom effects. Therefore, the inventions have a feature that the central metal M represented by general formula [formula 1] is iridium or platinum.

Further, in general formula [formula 1], the ligand L, which can be any one of a monoanionic ligand having a β-diketone structure, a monoanionic bidentate chelate ligand having a carboxyl group, or a monoanionic bidentate chelate ligand having a phenolic hydroxyl group, is preferably any one of monoanionic ligands represented by the following structural formulae [formula 2] to [formula 8]. These monoanionic bidentate chelate ligands have high coordination ability and are inexpensive, and so can be effectively used.

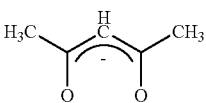

[formula 2]

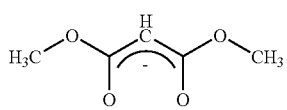

[formula 3]

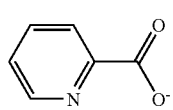

[formula 4]

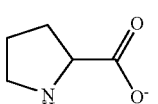

[formula 5]

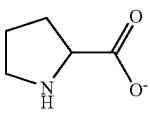

[formula 6]

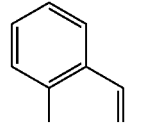

[formula 7]

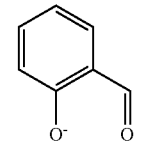

[formula 8]

The phosphorescent compounds according to the invention can cause the triplet excited energy to be emitted as light. Accordingly, the phosphorescent compounds are quite useful as a material for an electroluminescent device, since the efficiency of the electroluminescent device can be improved by applying the phosphorescent compounds thereto. Therefore, the inventions include an electroluminescent device containing phosphorescent compounds according to the invention.

Here, the phosphorescent compounds according to the invention may be used as a sensitizer as disclosed in Baldo et al.; however, they are used more effectively as a light emitter in terms of luminous efficiency. Therefore, the inventions include an electroluminescent device containing the phosphorescent compounds according to the invention as a light emitter.

Further, since the electroluminescent device according to the invention can achieve high luminous efficiency, the power consumption of a light-emitting device (an image display device or a light-emitting device) that uses the electroluminescent device as a light-emitting device can be reduced. Therefore, the inventions include a light-emitting device using the electroluminescent device according to the invention.

Note that the term "light-emitting device" in this specification refers to an image display device or a light-emitting device to which is applied an electroluminescent device as a light-emitting device. Further, the light-emitting device includes a module having an electroluminescent device attached with a connector such as an ACF (Anisotropic Conductive Film), an FPC (Flexible Printed Circuit), a TAB (Tape Automated Bonding), or a TCP (Tape Carrier Package); a module having an electroluminescent device attached with a TAB or a TCP provided with a printed wiring board at the end thereof; and a module having an organic light-emitting device installed directly with an IC (Integrated Circuit) by COG (Chip On Glass).

By practicing the invention, novel phosphorescent compounds can be provided. Further, by manufacturing an electroluminescent device with the phosphorescent compounds, an electroluminescent device having high luminous efficiency can be provided. Furthermore, by manufacturing a light-emitting device and an electric appliance by using the electroluminescent device, a light-emitting device and an electric appliance each of which consumes less power can be provided.

BRIEF DESCRIPTION OF THE DRAWINGS

FIG. 1 shows a device configuration of an electroluminescent device according to Embodiment 1;

FIG. 2 shows a device configuration of an electroluminescent device according to Embodiment 2;

FIG. 3 shows a device configuration of an electroluminescent device according to Embodiment 3;

FIG. 4A is an explanatory view of a light-emitting device;

FIG. 4B is a cross-sectional view of the light-emitting device of FIG. 4A, taken along the line A–A';

FIG. 6 is a graph for showing absorption, excitation, and emission spectra of the phosphorescent compound according to the present invention.

DETAILED DESCRIPTION OF THE PRESENTLY PREFERRED EMBODIMENTS

Figure 5A:
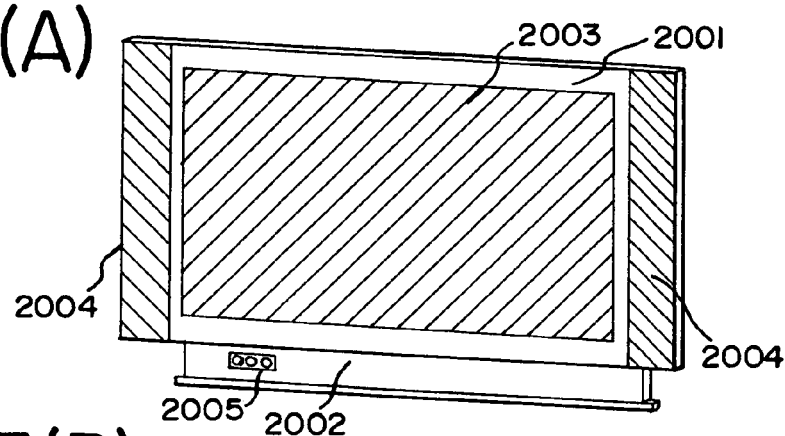
FIG. 5A to FIG. 5G are explanatory views of electric appliances.

Embodiments of the present invention will be explained hereinafter.

The ligand represented by general formula [formula 9] can be synthesized in accordance with synthesis scheme [scheme 10].

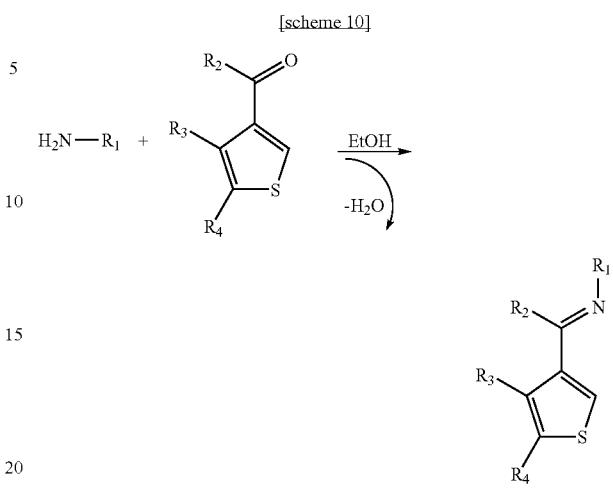

[scheme 10]

An orthometallated complex serving as a phosphorescent compound according to the invention is formed by using the obtained ligand represented by general formula [formula 9]. As an orthometallation reaction in this instance, a known synthesis method may be used.

For example, in order to synthesize a phosphorescent compound according to the invention having iridium as a central metal, an iridium chloride hydrate is used as central metal materials to be mixed with the ligand represented by general formula [formula 9], and the mixture is refluxed under a nitrogen atmosphere, then, a chloro-bridged dimer complex is synthesized (synthesis scheme [scheme 11] described below). And then, the obtained dimer complex and the ligand L are mixed and refluxed under a nitrogen atmosphere to split the chloro-bridge by the ligand L. Consequently, the phosphorescent compound according to the invention is obtained (synthesis [scheme 12]).

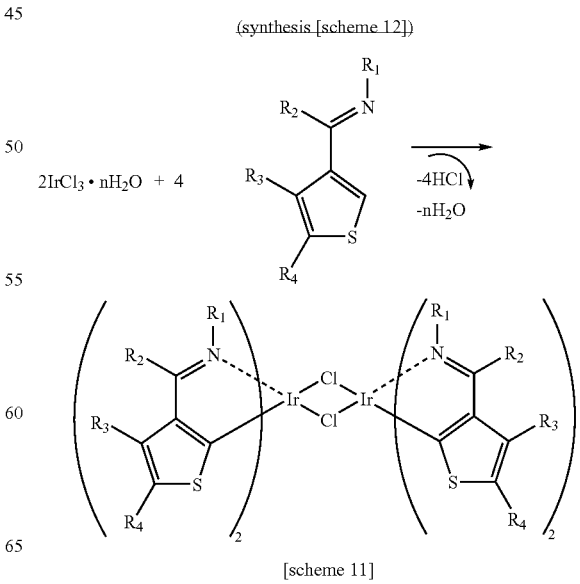

[scheme 11]

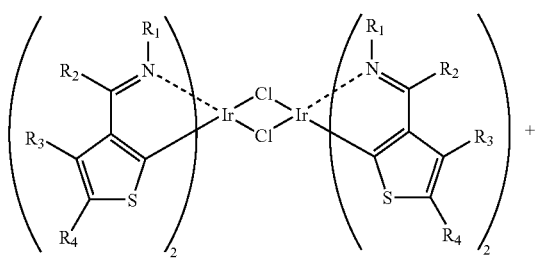

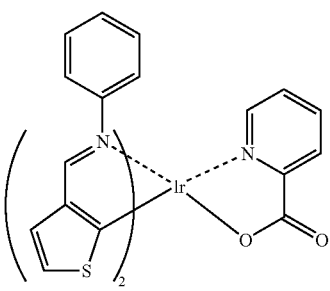

[formula 15]

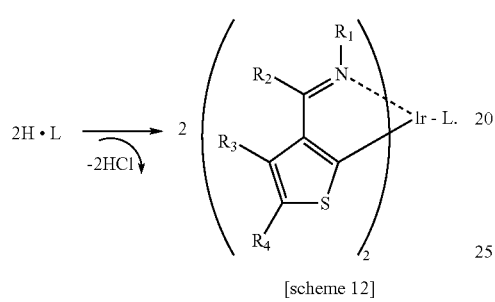

[scheme 12]

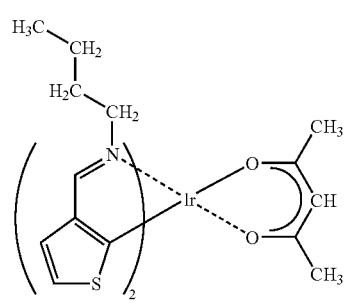

[formula 16]

The method for synthesizing a phosphorescent compound used in the invention is not limited to the above mentioned synthesis method.

Various emission colors can be obtained from the phosphorescent compound according to the invention by altering the construction of the ligand represented by general formula [formula 9]. Reference to the following structural formulae [formula 13] to [formula 17] can be made for specific examples. In addition, a phosphorescent compound used in the invention is not limited thereto.

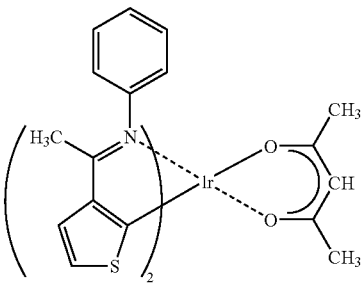

[formula 17]

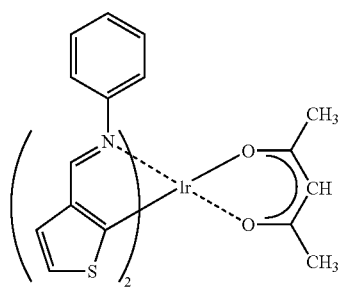

[formula 13]

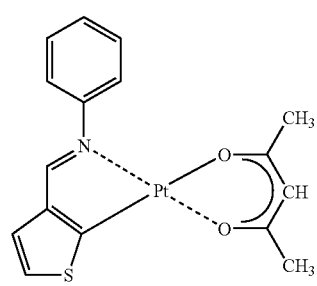

[formula 14]

The phosphorescent compound according to the invention can be used as a photosensitizer, phosphorescent material, or the like. Hereinafter, the case in which the phosphorescent compound according to the invention is applied to an electroluminescent device will be explained.

The electroluminescent device according to the invention has basically the device configuration in which an electroluminescent layer (a hole injecting layer, a hole transporting layer, a light-emitting layer, a blocking layer, an electron transporting layer, an electron injecting layer, and the like) containing the above mentioned phosphorescent compound according to the invention (represented by general formula [formula 1]) is interposed between a pair of electrodes (an anode and a cathode).

Also, as materials for the electroluminescent layer other than the phosphorescent compound according to the invention, either low molecular weight materials or high molecular weight materials can be used. Note that materials for forming a light-emitting layer may contain not only organic compounds but also inorganic compounds partly.

Hereinafter, embodiments of the electroluminescent device according to the invention will be explained in detail.

Embodiment 1

In Embodiment 1, a device configuration of an electroluminescent device which has a light-emitting layer containing phosphorescent compounds according to the invention; a hole injecting layer formed by low molecular weight materials; a hole transporting layer; a hole blocking layer; and an electron transporting layer will be explained with reference to FIG. 1.

As shown in FIG. 1, a first electrode 101 is formed over a substrate 100, and an electroluminescent layer 102 is formed over the first electrode 101, then, a second electrode 103 is formed thereover.

As materials for the substrate 100, anything can be used as long as it is used for the conventional electroluminescent device, for example, glass, quartz, transparent plastics, or the like.

In this embodiment, the first electrode 101 functions as an anode, and the second electrode 103 functions as a cathode.

Therefore, the first electrode 101 is formed by anode materials. As materials for the anode, metals having large work functions (at least 4.0 eV), alloys, compounds having electrical conduction properties, and mixtures of these materials can be preferably used. Note that, as specific examples of the anode materials, ITO (indium tin oxide), IZO (indium zinc oxide) composed of indium oxide mixed with zinc oxide (ZnO) of from 2 to 20%, gold (Au), platinum (Pt), nickel (Ni), tungsten (W), chrome (Cr), molybdenum (Mo), iron (Fe), cobalt (Co), copper (Cu), palladium (Pd), nitride of metal materials (TiN), or the like can be used.

Otherwise, as cathode materials for forming the second electrode 103, metals having small work functions (at most 3.8 eV), alloys, compounds having electrical conduction properties, mixtures of these materials, or the like is preferably used. Note that as specific examples of the cathode materials, an element of group 1 or 2 in the periodic table, that is, an alkali metal such as Li, Cs, or the like; alkaline earth metal such as Mg, Ca, Sr, or the like; alloys of these elements (Mg:Ag, Al:Li); compounds (LiF, CsF, CaF$_2$); or transition metals containing rare earth metals can be used. Alternatively, the second electrode 103 can be formed by stacking metals such as Al, Ag, or ITO (including alloys) with the foregoing materials.

The above anode and cathode materials are deposited by vapor deposition, sputtering, or the like to form thin films as the first electrode 101 and the second electrode 103. These electrodes preferably have thicknesses in a range of 10 to 500 nm, respectively.

Also, in the electroluminescent device according to the invention, light generated by recombination of carriers within the electroluminescent layer is emitted outside from either the first electrode 101 or the second electrode 103, or both of the electrodes. When light is emitted from the first electrode 101, the first electrode 101 is formed by materials having light transmission properties. When light is emitted from the second electrode 103, the second electrode 103 is formed by materials having light transmission properties.

The electroluminescent layer 102 is formed by stacking a plurality of layers. In this embodiment, the electroluminescent layer 102 is formed by stacking a hole injecting layer 111, a hole transporting layer 112, a light-emitting layer 113, a hole blocking layer 114, and an electron transporting layer 115.

As hole injection materials for forming the hole injecting layer 111, phthalocyanine-based compounds can be efficient. For example, phthalocyanine (abbreviated H$_2$—Pc), copper phthalocyanine (abbreviated Cu—Pc), or the like can be used.

As hole transportation materials for forming the hole transporting layer 112, aromatic amine (that is, the one having a benzene ring-nitrogen bond) based compounds are preferably used. For example, 4,4'-bis[N-(3-methylphenyl)-N-phenyl-amino]-biphenyl (abbreviated TPD) and derivatives thereof such as 4,4'-bis[N-(1-naphthyl)-N-phenyl-amino]-biphenyl (abbreviated a-NPD), are widely used. Also used are star burst aromatic amine compounds, such as 4,4',4''-tris(N,N-diphenyl-amino)-triphenyl amine (abbreviated TDATA) and 4,4',4''-tris[N-(3-methylphenyl)-N-phenyl-amino]-triphenyl amine (abbreviated MTDATA).

The light-emitting layer 113 contains the orthometallated complex represented above by general formula [formula 1]. The light-emitting layer 113 is formed by co-evaporating the orthometallated complex and host materials. Known materials can be used as the host materials, for example, 4,4'-bis(N-carbazolyl)-biphenyl (abbreviated CBP), 2,2',2''-(1,3,5-benzenetri-yl)-tris[1-phenyl-1H-benzimidazole] (abbreviated TPBI), or the like can be used.

As hole blocking materials for forming the hole blocking layer 114, bis(2-methyl-8-quinolinolate)-4-phenylphenolato-aluminum (abbreviated BAlq); 1,3-bis[5-(p-tert-butylphenyl)-1,3,4-oxadiazole-2-yl] benzene (abbreviated OXD-7); 3-(4-tert-butylphenyl)-4-phenyl-5-(4-biphenylyl)-1,2,4-triazole (abbreviated TAZ); 3-(4-tert-butylphenyl)-4-(4-ethylphenyl)-5-(4-biphenylyl)-1,2,4-triazole (abbreviated p-EtTAZ); bathophenanthroline (abbreviated BPhen); bathocuproin (abbreviated BCP); or the like can be used.

As electron transportation materials for forming the electron transporting layer 115, a metal complex having quinoline skeletons or benzoquinoline skeletons such as tris(8-quinolinolate) aluminum (abbreviated Alq$_3$), tris(5-methyl-8-quinolinolate) aluminum (abbreviated Almq$_3$), bis(10-hydroxybenzo[h]-quinolinato) beryllium (abbreviated BeBq$_2$), or the above mentioned BAlq are preferably used. Alternatively, a metal complex having oxazole based or thiazole based ligand such as bis [2-(2-hydroxyphenyl)-benzooxazolate] zinc (abbreviated Zn(BOX)$_2$) or bis [2-(2-hydroxyphenyl)-benzothiazolate] zinc (abbreviated Zn(BTZ)$_2$) can be used. In addition to a metal complex, 2-(4-biphenyl)-5-(4-tert-butylphenyl)-1,3,4-oxadiazole (abbreviated PBD); the above mentioned OXD-7; TAZ; p-EtTAZ; BPhen; BCP; or the like can be used.

Accordingly, an electroluminescent device which has the light-emitting layer 113 containing the phosphorescent compound according to the invention; the hole injecting layer 111 formed by low molecular weight materials; the hole transporting layer 112; the hole blocking layer 114; and the electron transporting layer 115 can be formed.

Note that the electroluminescent device according to Embodiment 1 having the light-emitting layer 113 which contains phosphorescent compounds according to the invention as guest materials emits light in the color obtained from the phosphorescent compound.

Embodiment 2

In Embodiment 2, the device configuration of an electroluminescent device which has a light-emitting layer containing the phosphorescent compound according to the invention and a hole injecting layer formed by polymer materials, each of which is formed by a wet process, will be explained with reference to FIG. 2.

In addition, a substrate 200, a first electrode 201, and a second electrode 203 can be formed by the same materials and in accordance with the same procedure as those explained in Embodiment 1, and will not be further explained in Embodiment 2.

Further, an electroluminescent layer 202 is formed by stacking a plurality of layers. In Embodiment 2, the electroluminescent layer 202 is formed by stacking a hole injecting layer 211 and a light-emitting layer 212.

As materials having hole injection properties for forming the hole injecting layer 211, polyethylene dioxythipophene (abbreviated PEDOT) doped with polystyrene sulfonate (abbreviated PSS), polyaniline, polyvinyl carbazole (abbreviated PVK), or the like can be used.

The light-emitting layer 212 contains the phosphorescent compound according to the invention represented by general formula [formula 1] as guest materials. Bipolar materials may be used as host materials, which may be formed by mixing hole transporting materials and electron transporting materials. Here, a solution is prepared in accordance with the procedure, that is, high molecular weight compounds (for example, PVK) having hole transportation properties and the above mentioned electron transporting materials (for example, PBD) are dissolved in the same solvent at 7:3 mol ratio, and an appropriate amount of the phosphorescent compounds according to the invention (approximately 5 wt %) is added. The solution is wet-coated to form the light-emitting layer 212.

Accordingly, an electroluminescent device which has the light-emitting layer 212 containing the phosphorescent compound according to the invention and the hole injecting layer 211 formed by high molecular weight materials, each of which is formed by wet processes, can be obtained.

Embodiment 3

In Embodiment 3, the device configuration of an electroluminescent device which has a light-emitting layer containing both the phosphorescent compounds according to the invention and fluorescent compounds; a hole injecting layer formed by low molecular weight materials; a hole transporting layer; a hole blocking layer; and an electron transporting layer will be explained with reference to FIG. 3.

In addition, a substrate 300, a first electrode 301, a second electrode 303, a hole injecting layer 311, a hole transporting layer 312, a hole blocking layer 314, and an electron transporting layer 315 can be formed by the same materials and in accordance with the same procedure as those explained in Embodiment 1, and will not be further explained in Embodiment 3.

The light-emitting layer 313 according to this Embodiment is formed by host materials; the phosphorescent compound according to the invention as the first guest materials; and fluorescent materials as the second guest materials. As the host materials, materials described in Embodiment 1 may be used.

As the second guest materials, known fluorescent compounds can be used. Specifically, DCM1, DCM2, DCJTB, quinacridone, N,N-dimethylquinacridone, rubrene, perylene, DPT, Co-6, PMDFB, BTX, ABTX, or the like can be used.

In Embodiment 3, as in Baldo et al., the phosphorescent compounds according to the invention used as the first guest materials serve as a sensitizer to amplify the number of the singlet excited state of the fluorescent compounds used as the second guest materials. Therefore, the electroluminescent device according to Embodiment 3 emits light in the color obtained from the fluorescent compounds. Further, the luminous efficiency of the fluorescent compounds according to Embodiment 3 can be further improved than that of the conventional fluorescent compounds.

EXAMPLES

Synthesis Example 1

In Synthesis Example 1, a method for synthesizing the phosphorescent compounds according to the invention represented by structural formula [formula 13] will be exemplified. The ligand raw material (yellow liquid) represented by structural formula [formula 18] was obtained by refluxing 3-thiophenecarboxyaldehyde with an equimolar amount of aniline in ethanol for 4 hours, and the solvent was removed.

[formula 18]

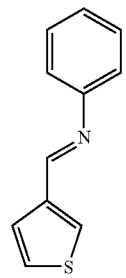

Then, the dimer complex represented below by structural formula [formula 19] was obtained by refluxing iridium chloride (IrCl$_3$.HCL.H$_2$O) with 2.5 equivalents of the ligand raw material represented by structural formula [formula 18] in a 3:1 mixture of 2-ethoxyethanole and water for 18 hours. Obtained powder was filtered off, and washed with ethanol and acetone, then, air-dried.

[formula 19]

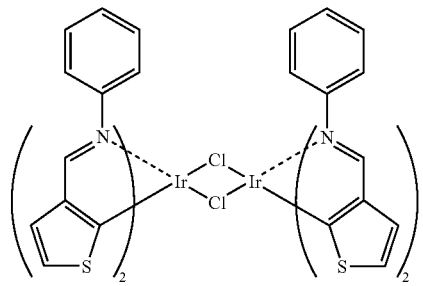

And then, the dimer complex represented by structural formula [formula 19], 3 equivalents of acetylacetone, and 10 equivalents of sodium carbonate were refluxed in 2-ethoxyethanole in a nitrogen atmosphere for 18 hours. After removing the solvent, the product was passed through an open column with dichloromethane for purification, and recrystallized from chloroform/hexane. The compound represented by formula [formula 13], which is an object of the present invention, was obtained.

FIG. 6 shows an absorption spectrum, an excitation spectrum, and an emission spectrum (PL) of the obtained phosphorescent compound (structural formula [formula 13])

according to the invention. FIG. 6 also shows an absorption spectrum of the ligand raw material (structural formula [formula 18]).

As shown in FIG. 6, compared with the spectrum ① of the ligand raw material, an absorption spectrum ② has a shoulder at long-wavelength side (around 340 nm, and from 350 to 400 nm), which suggests a triplet π-π* transition and a triplet MLCT transition. The position of an absorption spectrum ③ coincides with the positions of these triplet excitations. Accordingly, it can be considered that a triplet excited state excites luminescence. Therefore, it indicates that the compound according to the invention is a phosphorescent compound. In addition, an emission spectrum 4 shows bluish-purple emission having a peak at around 425 nm.

Synthesis Example 2

In Synthesis Example 2, a method for synthesizing the phosphorescent compound according to the invention represented by structural formula [formula 15] will be exemplified. Firstly, the dimer complex represented by structural formula [formula 19] was obtained in accordance with the procedure conducted in Synthesis Example 1.

Then, the dimer complex represented by structural formula [formula 19], 3 equivalents of picolinic acid, and 10 equivalents of sodium carbonate were refluxed in 2-ethoxyethanole in a nitrogen atmosphere for 18 hours. After removing the solvent, the product was passed through an open column with dichloromethane for purification, and recrystallized from chloroform/hexane. The compound represented by formula 15, a compound according to an object of the present invention, was obtained.

Figure 7:
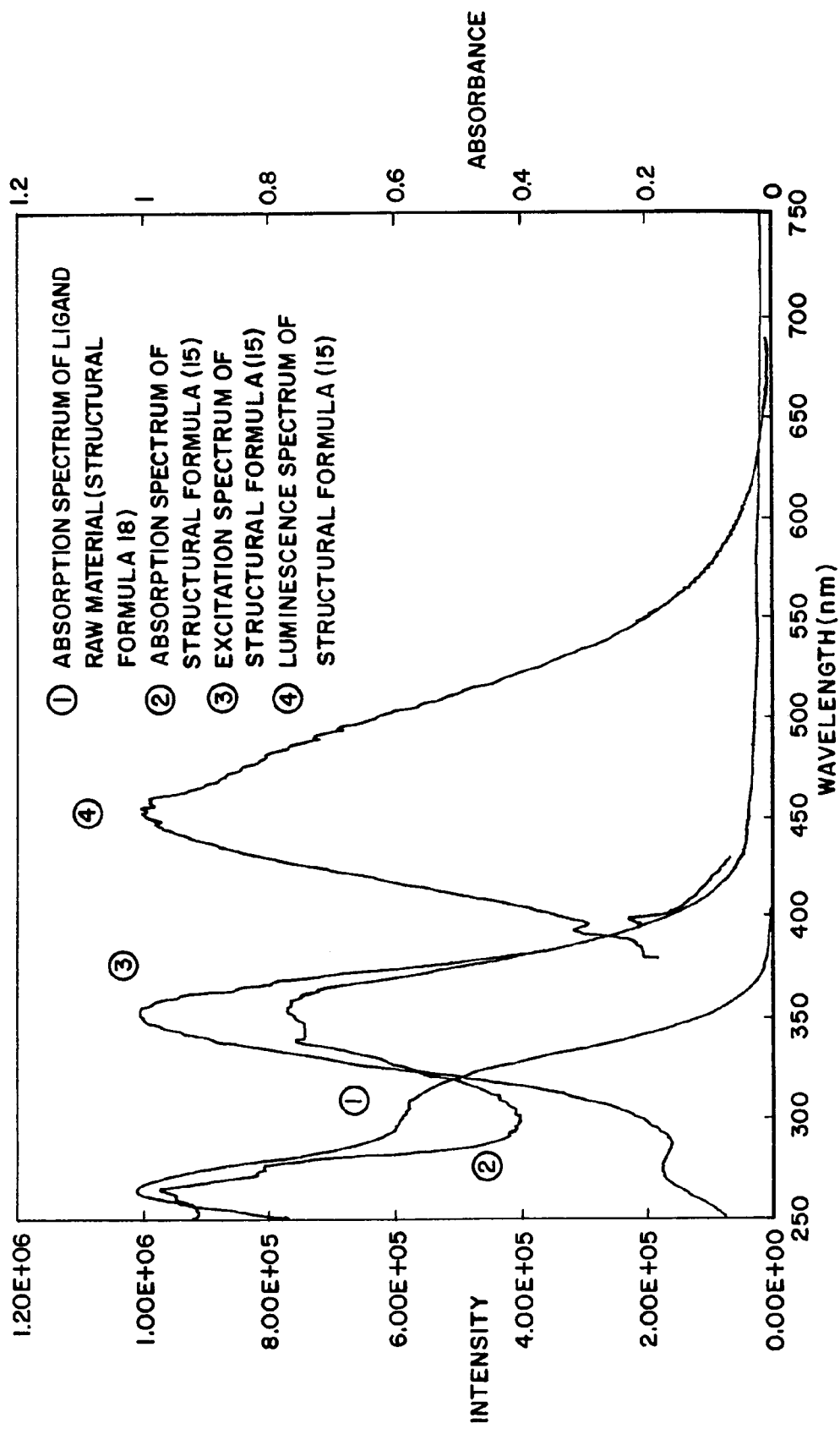
FIG. 7 is a graph for showing absorption, excitation, and emission spectra of the phosphorescent compound according to the invention.

FIG. 7 shows an absorption spectrum, an excitation spectrum, and an emission spectrum (PL) of the obtained phosphorescent compound (structural formula 15) according to the invention. FIG. 7 also shows an absorption spectrum of ligand raw materials (structural formula [formula 18]).

As shown in FIG. 7, compared with the spectrum ① of the ligand raw materials, an absorption spectrum ② has two peaks at long-wavelength side (around from 340 to 370 nm), which suggests a triplet π-π* transition and a triplet MLCT transition. The position of an absorption spectrum ③ coincides with the positions of these triplet excitations. Accordingly, it can be considered that a triplet excited state excites the luminescence. Therefore, it indicates that the compound according to the invention is a phosphorescent compound. In addition, an emission spectrum ④ shows blue emission having a peak at around 450 nm.

Example 1

Hereinafter, a light-emitting device having a pixel portion composed of the electroluminescent devices according to the invention will be explained with reference to FIG. 4A and FIG. 4B. FIG. 4A is a top view of the light-emitting device. FIG. 4B is a cross-sectional view of FIG. 4A taken along the line A–A'. Reference numeral 401 shown by a dotted line denotes a driver circuit portion (a source driver circuit), 402 denotes a pixel portion, and 403 denotes a driver circuit portion (a gate side driver circuit). Further, reference numeral 404 denotes a sealing substrate, 405 denotes a sealing agent and 407 denotes space surrounded by the sealing agent 405.

Further, reference numeral 408 denotes a wiring for transmitting signals, which are inputted to the source signal line driver circuit 401 and the gate signal line driver circuit 403. The wiring receives video signals, clock signals, start signals, reset signals, and the like from an FPC (Flexible Print Circuit) 409, which serves as an external input terminal. Though only FPC is illustrated here, the FPC can be provided with a print wiring board (PWB). As used herein, the term "light-emitting device" refers to not only a main body of the light-emitting device but also the one provided with an FPC or a PWB.

The cross-sectional structure is described with reference to FIG. 4B. A driver circuit portion and a pixel portion are formed over a substrate 410. Here, a source driver circuit 401 serving as a driver circuit portion and a pixel portion 402 are illustrated.

In the source driver circuit 401, a CMOS circuit composed of an n-channel TFT 423 and a p-channel TFT 424 is formed. Also, the TFT for forming a driver circuit may be formed by a known CMOS circuit, PMOS circuit, or NMOS circuit. In this embodiment, a driver integrated type in which a driver circuit is formed over a substrate is illustrated. However, the driver circuit can also be formed outside instead of over a substrate.

The pixel portion 402 is formed by a plurality of pixels having a switching TFT 411, a current control TFT 412, and a first electrode (anode) 413 connected electrically to the drain of the current control TFT 412. Further, an insulator 414 is formed to cover the edge of the first electrode 413. Here, the insulator 414 is formed by a positive type photosensitive acrylic resin film.

Also, for improving the coverage, the upper edge portion or the lower edge portion of the insulator 414 is formed to have a curved surface having a radius of curvature. For example, when a positive photosensitive acrylic resin film is used for forming the insulator 414, only the upper edge portion of the insulator 414 is preferably formed to have a curved surface having a radius of curvature (0.2 to 3 μm). Also, as materials for the insulator 414, either a negative type photosensitive resin that becomes insoluble to etchant by light or a positive type photosensitive resin that becomes dissoluble to etchant by light can be used.

An electroluminescent layer 416 and a second electrode 417 are formed over the first electrode 413, respectively. As a material for the first electrode 413 serving as an anode, a material having a large work function is preferably used. For instance, the first electrode 413 can be formed by a single layer such as an ITO (indium tin oxide) film, an IZO (indium zinc oxide) film, a titanium nitride film, a chromic film, a tungsten film, a Zn film, or a Pt film; a lamination layer having one of the above single layer and a film containing mainly titanium nitride and aluminum; a three lamination layer having a titanium nitride film, a film containing aluminum as its main components, and another titanium nitride film; or the like. In case of adopting the lamination layer, the first electrode 413 can be formed to have low resistance as a wiring, make good ohmic contact, and serve as an anode.

The electroluminescent layer 416 is formed by vapor deposition using an evaporation mask, or ink jetting. The electroluminescent layer 416 partly contains the phosphorescent compound according to the invention (general formula 1). Besides, either low molecular weight materials or polymer materials can be used with the phosphorescent compound in combination. Also, generally, an electroluminescent layer is formed by a single layer or a lamination layer, each of which is formed by an organic compound; however, the electroluminescent layer 416 according to this embodiment can be formed to contain partly an inorganic compound.

Further, as materials for the second electrode (cathode) 417 formed over the electroluminescent layer 416, materials having a small work function (Al, Ag, Li, Ca, or alloys of the foregoing materials such as MgAg, MgIn, AlLi, $CaF_2$, or CaN) can be used. In case that light generated in the electroluminescent layer 416 passes through the second electrode (cathode) 417, the second electrode (cathode) 417 is preferably formed by a lamination layer composed of a thin metal film and a transparent conductive film (alloys such as indium tin oxide (ITO), indium zinc oxide ($In_2O_3$—ZnO), zinc oxide (ZnO), or the like).

The sealing substrate 404 is pasted onto the substrate 410 with the sealing agent 405 to encapsulate a light-emitting element 418 within the space 407 surrounded by the substrate 401, the sealing substrate 404, and the sealing agent 405. The invention comprehends not only the case that the space 407 is filled with an inert gas (such as nitrogen or argon) but also the case that the space 407 is filled with the sealing agent 405.

The sealing agent 405 is preferably formed by epoxy-based resin. In addition, it is desirable that the material for the sealing agent inhibits the penetration of moisture or oxygen as much as possible. As materials for the sealing substrate 404, a plastic substrate such as FRP (fiberglass-Reinforced Plastics), PVF (polyvinyl fluoride), Mylar®, polyester, or acrylic can be used besides a glass substrate or a quartz substrate.

Accordingly, a light-emitting device having the electroluminescent device according to the invention can be obtained.

Example 2

Hereinafter, various electric appliances that are completed by using a light-emitting device having the electroluminescent device according to the present invention will be explained.

Figure 5B:
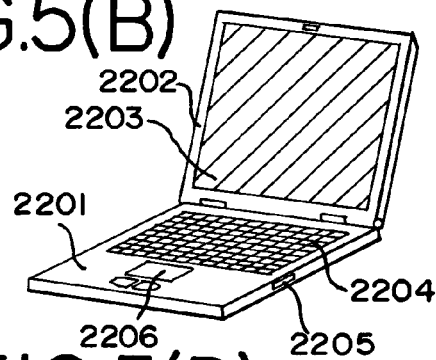

Given as examples of such electric appliances manufactured by using the light-emitting device having the electroluminescent devices according to the invention: a video camera, a digital camera, a goggles-type display (head mount display), a navigation system, a sound reproduction device (a car audio equipment, an audio set and the like), a laptop personal computer, a game machine, a portable information terminal (a mobile computer, a cellular phone, a portable game machine, an electronic book, or the like), an image reproduction device including a recording medium (more specifically, a device which can reproduce a recording medium such as a digital versatile disc (DVD), and so forth, and includes a display for displaying the reproduced image), or the like. FIG. 5A to FIG. 5B show various specific examples of such electric appliances.

FIG. 5A shows a display device composed of a casing 2001; a support 2002; a display portion 2003; a speaker unit 2004; a video input terminal 2005; and the like. The display device is manufactured by using the light-emitting device having the electroluminescent device according to the invention for the display portion 2003. The display device includes display devices for all information such as for a personal computer, TV broadcast reception, advertisement, and the like.

FIG. 5B shows a laptop computer composed of a main body 2201; a casing 2202; a display portion 2203; a keyboard 2204; an external connection port 2205; a pointing mouse 2206; and the like. The laptop computer is manufactured by using the light-emitting device having the electroluminescent device according to the invention for the display portion 2203.

Figure 5C:
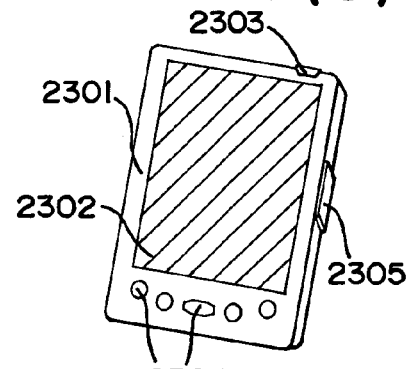

FIG. 5C shows a mobile computer composed of a main body 2301; a display portion 2302; operation keys 2304; an infrared port 2305; and the like. The mobile computer is manufactured by using the light-emitting device having the electroluminescent device according to the invention for the display portion 2302.

Figure 5D:
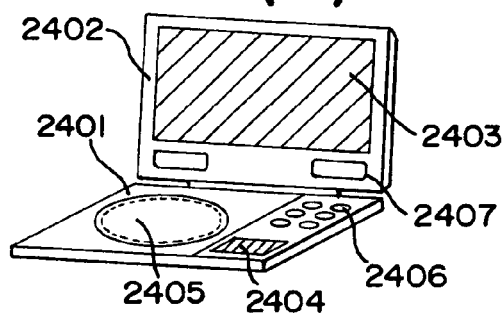

FIG 5D shows a portable image reproduction device including a recording medium (specifically, a DVD reproduction device) composed of a main body 2401; a casing 2402; a display portion A 2403; another display portion B 2404; a recording medium (DVD or the like) reading portion 2405; operation keys 2406; a speaker portion 2407; and the like. The display portion A 2403 is used mainly for displaying image information, while the display portion B 2404 is used mainly for displaying character information. The image reproduction device is manufactured by using the light-emitting device using the electroluminescent device according to the invention for the display potion A 2403 and the display portion B 2404. The image reproduction device including a recording medium further includes a home game machine, or the like.

Figure 5E:
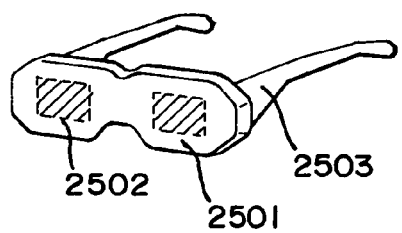

FIG. 5E shows a goggle type display (head mounted display) composed of a main body 2501; a display portion 2502; and an arm portion 2503. The goggle type display is manufactured by using the light-emitting device having the electroluminescent device according to the invention for the display portion 2502.

Figure 5F:
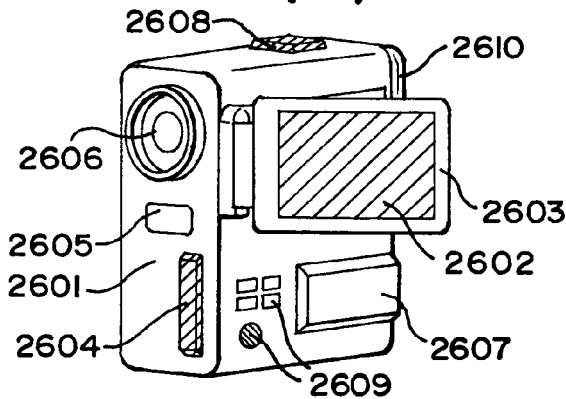

FIG 5F shows a video camera composed of a main body 2601; a display portion 2602; a casing 2603; an external connecting port 2604; a remote control receiving portion 2605; an image receiving portion 2606; a battery 2607; a sound input portion 2608; an operation key 2609; an eyepiece portion 2610; and the like. The video camera is manufactured by using the light-emitting device having the electroluminescent device according to the invention for the display portion 2602.

Figure 5G:
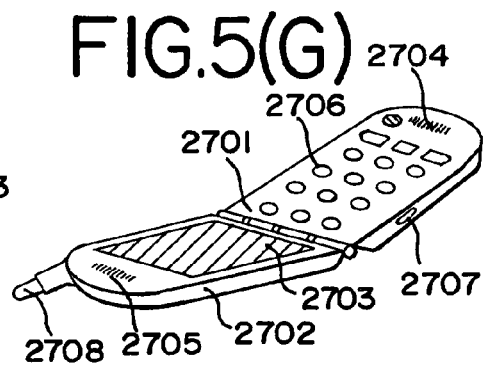

FIG. 5G shows a cellular phone composed of a main body 2701; a casing 2702; a display portion 2703; a sound input portion 2704; a sound output portion 2705; operation keys 2706; an external connecting port 2707; an antenna 2708; and the like. The cellular phone is manufactured by using the light-emitting device having the electroluminescent device according to the invention for the display portion 2703. The display portion 2703 can reduce power consumption of the cellular phone by displaying white-colored characters on a black-colored background.

As set forth above, the applicable range of the light-emitting device having the electroluminescent device according to the invention is extremely large, so that the light-emitting device can be applied to various fields' electric appliances.

What is claimed is:

1. A phosphorescent compound represented by general formula [formula 1]:

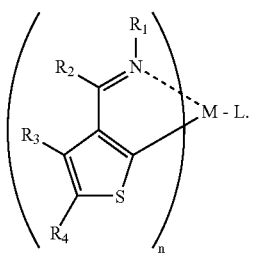

[formula 1]

wherein $R_1$ is an alkyl group, an aryl group, a substituted aryl group, a heterocyclic group, or a substituted heterocyclic group, Also, $R_2$ is hydrogen, an alkyl group, an aryl group, a substituted aryl group, a heterocyclic group, or a substituted heterocyclic group. Also, $R_3$ and $R_4$, each of which may be the same or different, are individually hydrogen, a halogen element, an alkyl group, an alkoxy group, an aryl group, a substituted aryl group, a heterocyclic group, or a substituted heterocyclic group. Also, M is at least one element of group 9 in the periodic table or at least one element of group 10 in the periodic table. When the M is at least one element of group 9 in the periodic table, n=2. When the M is at least one element of group 10 in the periodic table, n=1. Also, L is a monoanionic ligand having a β-diketone structure, a monoanionic bidentate chelate ligand having a carboxyl group, or a monoanionic bidentate chelate ligand having a phenolic hydroxyl group.

2. A phosphorescent compound according to claim 1, wherein the M is an iridium element or a platinum element.

3. A phosphorescent compound according to claim 1, wherein the L is a monoanionic ligand represented by structural formula [formula 2].

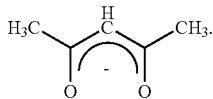

[formula 2]

4. A phosphorescent compound according to claim 1, wherein the L is a monoanionic ligand represented by structural formula [formula 3].

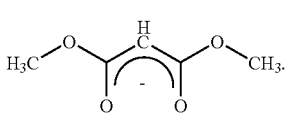

[formula 3]

5. A phosphorescent compound according to claim 1, wherein the L is a monoanionic ligand represented by structural formula [formula 4].

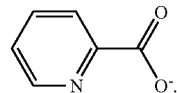

[formula 4]

6. A phosphorescent compound according to claim 1, wherein the L is a monoanionic ligand represented by structural formula [formula 5].

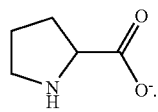

[formula 5]

7. A phosphorescent compound according to claim 1, wherein the L is a monoanionic ligand represented by structural formula [formula 6].

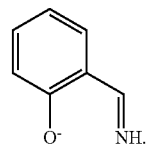

[formula 6]

8. A phosphorescent compound according to claim 1, wherein the L is a monoanionic ligand represented by structural formula [formula 7].

[formula 7]

9. A phosphorescent compound according to claim 1, wherein the L is a monoanionic ligand represented by structural formula [formula 8].

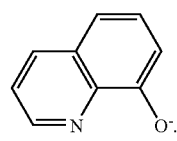

[formula 8]

10. An electroluminescent device having the phosphorescent compound according to claim 1.

11. An electroluminescent device using the phosphorescent compound according to claim 1 as a light emitter.

12. A light-emitting device having the electroluminescent device according to claim 10.

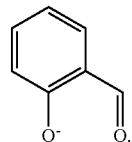

13. A light-emitting device having the electroluminescent device according to claim 11.

14. An electric appliance having the light-emitting device according to claim 12 in a display portion.

15. An electric appliance having the light-emitting device according to claim 13 in a display portion.

* * * * *